United States Patent
Shim et al.

(10) Patent No.: US 10,254,236 B2
(45) Date of Patent: Apr. 9, 2019

(54) METHODS OF MEASURING PATTERNS AND METHODS OF MANUFACTURING SEMICONDUCTOR DEVICES INCLUDING THE SAME

(71) Applicants: Sung-Bo Shim, Hwasung-si (KR); Jeonghoon Ko, Seoul (KR); Jehyun Lee, Suwon-si (KR); Jaehoon Jeong, Hwaseong-si (KR)

(72) Inventors: Sung-Bo Shim, Hwasung-si (KR); Jeonghoon Ko, Seoul (KR); Jehyun Lee, Suwon-si (KR); Jaehoon Jeong, Hwaseong-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 70 days.

(21) Appl. No.: 15/653,539

(22) Filed: Jul. 19, 2017

(65) Prior Publication Data
US 2018/0088060 A1    Mar. 29, 2018

(30) Foreign Application Priority Data
Sep. 23, 2016 (KR) .................. 10-2016-0122397

(51) Int. Cl.
G06T 7/13 (2017.01)
G01N 21/956 (2006.01)
(Continued)

(52) U.S. Cl.
CPC ... *G01N 21/95607* (2013.01); *G01N 23/2251* (2013.01); *G03F 7/70633* (2013.01); *G06T 7/001* (2013.01); *G06T 7/13* (2017.01); *G06T 7/136* (2017.01); *H01L 22/12* (2013.01); *H01L 22/34* (2013.01); *H01L 23/544* (2013.01); *G06T 2207/30148* (2013.01); *H01J 2237/221* (2013.01); *H01J 2237/2485* (2013.01); *H01L 27/11565* (2013.01); *H01L 27/11582* (2013.01)

(58) Field of Classification Search
USPC .......................................... 716/55
See application file for complete search history.

(56) References Cited

U.S. PATENT DOCUMENTS 7,379,185 B2  5/2008 Borden et al.
7,660,484 B2  2/2010 Ahn et al.
(Continued)

FOREIGN PATENT DOCUMENTS

KR   10-0747286 B1   8/2007
KR   10-0933819 B1   12/2009
(Continued)

*Primary Examiner* — Mohammed Alam
(74) *Attorney, Agent, or Firm* — Volentine, Whitt & Francos, PLLC

(57) ABSTRACT

A method of inspecting patterns formed the manufacturing of semiconductor devices or the like includes producing an image of the patterns, producing a boundary image including a plurality of boundary patterns corresponding to first and second boundaries of each of the patterns, combining the pattern image and the boundary image to produce an overlapping image including overlapping patterns in which the patterns fill regions between the boundary patterns, and binarizing the overlapping image to produce a binary image including binary patterns corresponding to the overlapping patterns.

20 Claims, 21 Drawing Sheets

(51) Int. Cl.
*G03F 7/20* (2006.01)
*G06T 7/00* (2017.01)
*H01L 21/66* (2006.01)
*H01L 23/544* (2006.01)
*G06T 7/136* (2017.01)
*G01N 23/2251* (2018.01)
*H01L 27/11582* (2017.01)
*H01L 27/11565* (2017.01)

(56) References Cited

U.S. PATENT DOCUMENTS

| | | | |
|---|---|---|---|
| 7,940,995 B2 | 5/2011 | Lee et al. | |
| 7,999,867 B2 | 8/2011 | Noh | |
| 8,014,584 B2 | 9/2011 | Matsumoto | |
| 8,159,552 B2 | 4/2012 | Lim et al. | |
| 8,248,662 B2 | 8/2012 | Seo | |
| 8,606,016 B2 | 12/2013 | Hou et al. | |
| 8,923,610 B2 | 12/2014 | Guo et al. | |
| 9,140,539 B2 | 9/2015 | Scheiner | |
| 9,245,349 B2 | 1/2016 | Heo | |
| 2013/0321671 A1* | 12/2013 | Cote | H04N 5/365 348/241 |
| 2013/0321672 A1* | 12/2013 | Silverstein | H04N 5/365 348/241 |
| 2013/0321679 A1* | 12/2013 | Lim | H04N 5/23229 348/256 |
| 2013/0329098 A1* | 12/2013 | Lim | H04N 9/64 348/246 |
| 2014/0133749 A1* | 5/2014 | Kuo | G06T 7/408 382/167 |
| 2018/0088060 A1* | 3/2018 | Shim | G01N 21/95607 |

FOREIGN PATENT DOCUMENTS

| | | |
|---|---|---|
| KR | 10-1015646 B1 | 2/2011 |
| KR | 10-1180059 B1 | 9/2012 |
| KR | 10-1440293 B1 | 8/2013 |
| KR | 10-1399012 B1 | 5/2014 |
| KR | 10-2014-0096880 A | 8/2014 |

\* cited by examiner

METHODS OF MEASURING PATTERNS AND METHODS OF MANUFACTURING SEMICONDUCTOR DEVICES INCLUDING THE SAME

PRIORITY STATEMENT

This U.S. nonprovisional patent application claims priority under 35 U.S.C. § 119 of Korean Patent Application 10-2016-0122397 filed on Sep. 23, 2016 entire contents of which are hereby incorporated by reference.

BACKGROUND

The present inventive concept relates to the manufacturing of semiconductor devices or the like. More particularly, the present inventive concept relates to a method of inspecting a pattern using an electron microscope and to a method of manufacturing a semiconductor device including the same.

In general, a semiconductor device may be manufactured by unit processes such as a thin film deposition process, a photolithography process, and an etching process. An inspection process may increase production yield by determining whether the unit processes have been performed normally or abnormally. For example, the inspection process may be executed using an optical or electron microscope.

SUMMARY

According to the present inventive concept there is provided of a method of measuring a pattern, comprising producing a pattern image of patterns, wherein the patterns contained in the pattern image each correspond to a respective one of patterns being inspected and each have first and second boundaries, producing a boundary image including a plurality of boundary patterns corresponding to the first and second boundaries, combining the pattern image and the boundary image to produce an overlapping image including overlapping patterns in which images of the patterns contained in the image pattern occupy regions between the boundary patterns, and binarizing the overlapping image to produce a binary image including binary patterns corresponding to the overlapping patterns.

According to the present inventive concept there is provided a method of manufacturing a semiconductor device, comprising forming a thin-layer structure on a substrate, etching a portion of the thin-layer structure to form channel holes, and inspecting the channel holes to determine whether the channel holes have been formed normally. The channel holes are inspected using an electron microscope to produce a pattern image of patterns. The patterns contained in the pattern image each correspond to a respective one of the channel holes and each have first and second boundaries. A boundary image is produced and includes a plurality of boundary patterns corresponding to the first and second boundaries. The pattern image and the boundary image are combined to produce an overlapping image including overlapping patterns in which images of the channel holes contained in the image pattern occupy regions between the boundary patterns. Then the overlapping image is binarized to produce a binary image including binary patterns corresponding to the overlapping patterns.

According to the present inventive concept, there is also provided a method of manufacturing a semiconductor device, comprising forming patterns on a substrate, imaging the substrate to produce a pattern image containing images representative of the patterns, respectively, each of the images having discernible regions demarcated by first and second boundaries, enhancing the pattern image to produce a boundary image, wherein the boundary image includes boundary patterns as image enhancements of the first and second boundaries demarcating the regions of the images contained in the pattern image, digitally combining the pattern image and the boundary image to produce an overlapping image, wherein the overlapping image includes overlapping patterns representative of a superimposing of the images contained in the pattern image with the boundary patterns, respectively, producing a binary image of the overlapping image, wherein the binary image includes binary patterns corresponding to the overlapping patterns, and analyzing the binary image to determine whether the patterns have been formed according to specifications on the substrate

DETAILED DESCRIPTION

Figure 1:
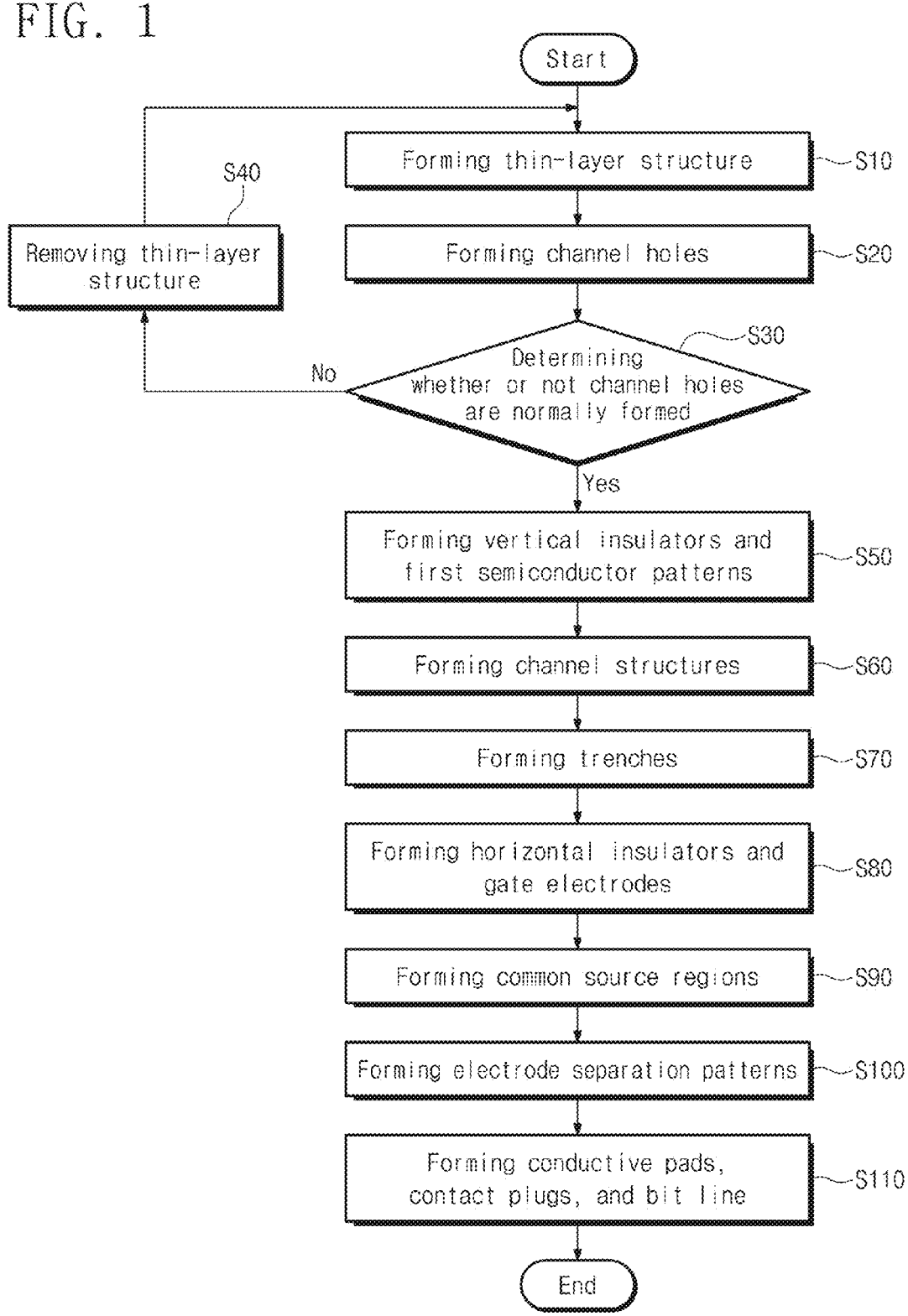
FIG. 1 is flow chart illustrating a method of manufacturing a semiconductor device according to examples of the present inventive concept.

FIG. 1 is flow chart of examples of a method of manufacturing a semiconductor device according to the present inventive concept.

Referring to FIG. 1, a method of manufacturing a semiconductor device may include forming a thin-layer structure (S10), forming channel holes (S20), determining whether the channel holes have been formed normally (S30), removing the thin-layer structure when the channel holes have not been formed normally (S40), and when the channel holes have been formed normally forming vertical insulators and first semiconductor patterns (S50), forming second semiconductor patterns and vertical insulation patterns (S60), forming trenches (S70), forming horizontal insulators and gate electrodes (S80), forming common source regions (S90), forming electrode separation patterns (S100), and forming conductive pads, contact plugs, and a bit line (S110). As will be described in more detail later on, operation (S40) may be part of a re-fabricating routine, whereas any or all of operations (S50)-(S110) may constitute a manufacturing routine for completing the semiconductor device.

FIGS. 2A to 2J are cross-sectional views illustrating a method of manufacturing a semiconductor device according to the flow of FIG. 1.

Figure 2A:
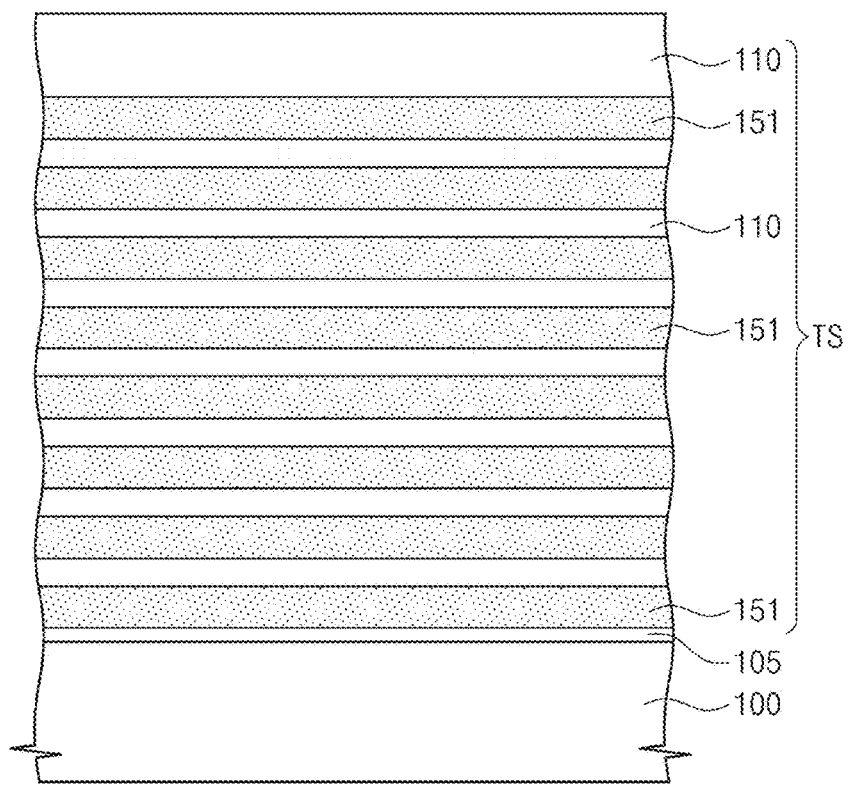
FIGS. 2A, 2B, 2C, 2D, 2E, 2F, 2G, 2H, 2I and 2J are cross-sectional views illustrating a semiconductor device during the course of its manufacturing according to the method of FIG. 1, and where FIG. 2C includes a schematic diagram of an image processing unit.

Referring to FIGS. 1 and 2A, a thin-layer structure TS may be formed on a substrate 100 (S10). For example, the substrate 100 may include silicon, germanium, or silicon-germanium. A lower insulation layer 105 may be formed on the substrate 100 so as to be provided between the substrate 100 and the thin-layer structure TS. In an example, the lower insulation layer 105 may include silicon oxide. A thermal oxidation process may be performed to form the lower insulation layer 105. Alternatively, a chemical vapor deposition process may be performed to form the lower insulation layer 105.

The thin-layer structure TS may be thicker than the lower insulation layer 105. In an example, the thin-layer structure TS may include sacrificial layers 151 and upper insulation layers 110. The sacrificial layers 151 and the upper insulation layers 110 may be alternately formed. Each of the sacrificial layers 151 and the upper insulation layers 110 may be formed thicker than the lower insulation layer 105.

The sacrificial layers 151 may be formed of a material that can be etched with an etch selectivity to the upper insulation layers 110. In an example, the sacrificial layers 151 and the upper insulation layers 110 may exhibit a high wet etch selectivity to a chemical solution and a low dry etch selectivity to an etching gas. The sacrificial layers 151 and the upper insulation layers 110 may be formed of insulating materials having etch selectivities different from each other. For example, the sacrificial layers 151 may include at least one of polysilicon, silicon oxide, silicon carbide, silicon oxynitride, and silicon nitride. In an example, the sacrificial layers 151 may have the same thickness. Alternatively, lowermost and uppermost ones of the sacrificial layers 151 may be formed thicker than others of the sacrificial layers 151 interposed therebetween. The upper insulation layers 110 may have the same thicknesses, but alternatively one or more of the upper insulation layers 110 may have a different thickness(es) than the other the upper insulation layer(s) 110.

The upper insulation layers 110 may be deposited using a thermal chemical vapor deposition (CVD) process, a plasma enhanced CVD process, a physical CVD process, or an atomic layer deposition (ALD) process. The upper insulation layers 110 may include at least one of polysilicon, silicon oxide, silicon carbide, silicon oxynitride, and silicon nitride, which material is different from that of the sacrificial layers 151. For example, the sacrificial layers 151 may include silicon nitride. The upper insulation layers 110 may include silicon oxide. Alternatively, the sacrificial layers 151 may include a conductive material and the upper insulation layers 110 may include an insulating material. An uppermost one of the upper insulation layers 110 may be formed above the uppermost one of the sacrificial layers 151.

Figure 2B:
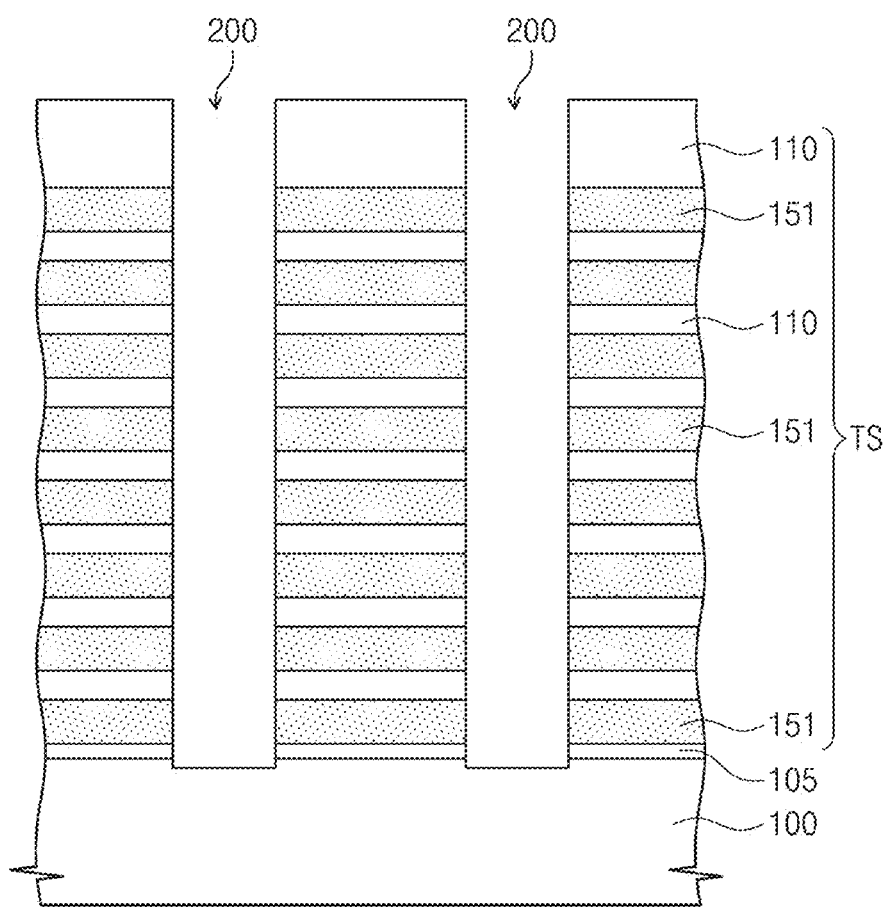

Referring to FIGS. 1 and 2B, channel holes 200 may be formed in the thin-layer structure TS (S20). In an example, the channel holes 200 may be formed by a photolithography process and an etching process on the thin-layer structure TS. The photolithography process may include forming a first mask pattern (not shown) having openings in corresponding to the channel holes 200. The first mask pattern may include a material having an etch selectivity to the sacrificial layers 151 and the upper insulation layers 110. For example, the first mask pattern may include a photoresist or hardmask pattern. The etching process may be performed to anisotropically remove portions of the thin-layer structure TS exposed by the openings of the first mask pattern. The etching process may include a dry etching process. For example, the etching process may form the channel holes 200 to each have a width at its lower portion substantially the same as that at its upper portion. During the etching process, the top surface of the substrate 100 may be partially etched. Accordingly, the top surface of the substrate 100 may be recessed. Alternatively, the etching process may form each channel hole 200 to have a width at its lower portion less than that at its upper portion. Subsequently, the first mask patterns may be removed.

Figure 2C:
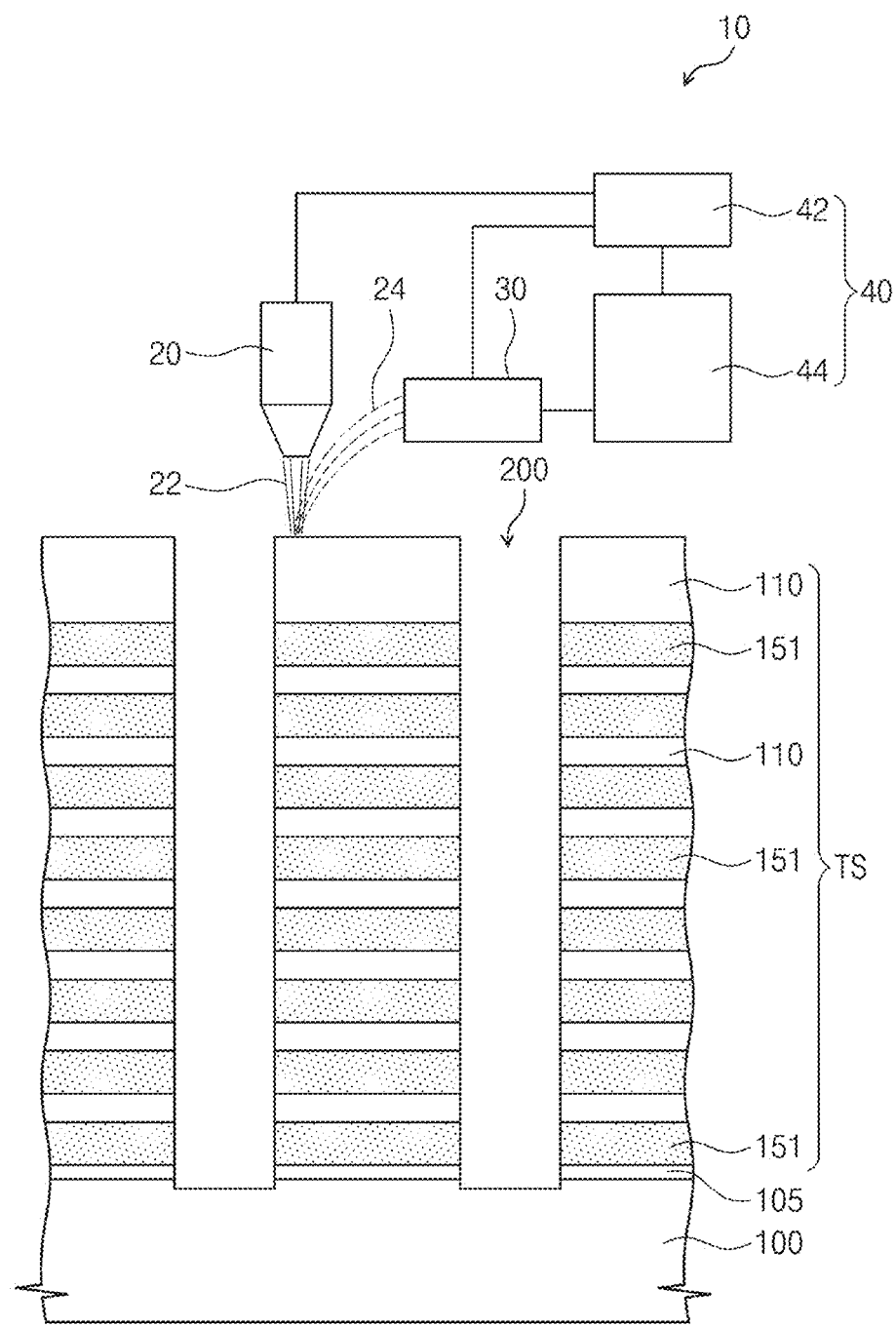

Referring to FIGS. 1 and 2C, the channel holes 200 may be measured or inspected to determine whether the channel holes 200 have been formed normally (S30). For example, the channel holes 200 may be measured by an electron microscope 10. In an example, the electron microscope 10 may include an electron beam providing unit 20, a detection unit 30, and a controller 40.

The electron beam providing unit 20 may direct an electron beam 22 to the thin-layer structure TS and the substrate 100. The electron beam providing unit 20 may be an electron beam source. For example, the electron beam 22 may have energy in the range of from about 0.1 eV to about 1,000 eV. Here, the term "about" is intended to encompass not only the precise range of 0.1 eV to about 1,000 eV but also slight variations due to inherent characteristics of the electron beam providing unit 20 or processing conditions. Secondary electrons 24 may be produced from the thin-layer structure TS exposed to, i.e., irradiated by, the electron beam 22.

The detection unit 30 may be provided above the thin-layer structure TS. The detection unit 30 may detect the produced secondary electrons 24. For example, the detection unit 30 may include a positively charged electrode. The secondary electrons 24 may be collected on the detection unit 30 by an electrostatic force.

The controller 40 may be configured to control the electron beam providing unit 20 and the detection unit 30. Alternatively, the controller 40 may be configured to receive a detection signal from the detection unit 30 and process images according to the detection signal. For example, the controller 40 may include a processor or a field-programmable gate array (FPGA). In an example, the controller 40 may include a drive controlling part 42 and an image processor 44.

The drive controlling part 42 may drive the electron beam providing unit 20 and the detection unit 30. For example, the drive controlling part 42 may include an operation processor section and a control output section.

The image processor 44 (referred to hereinafter as image processing part 44 of the electron microscope 10) may receive a detection signal from the detection unit 30. The image processing part 44 may analyze a detection signal representative of the channel holes 200. For example, the image processing part 44 may include a graphic control section and a graphic analysis section.

The substrate 100 may be moved by a stage (not shown) of the electron microscope 10. The stage may be controlled by the drive controlling part 42.

Figure 3:
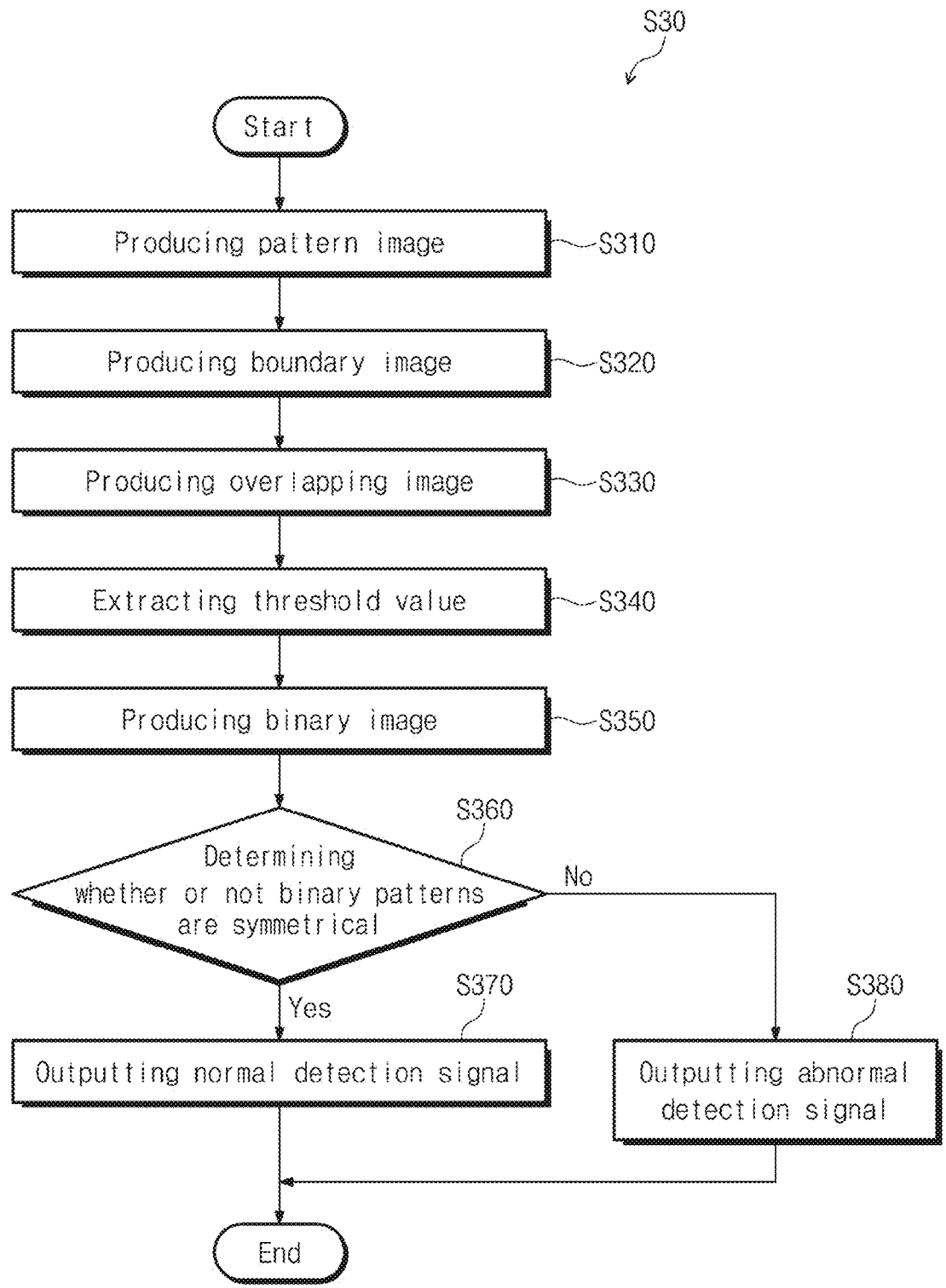
FIG. 3 is a flow chart illustrating an example of a routine of determining whether channel holes have been normally formed when implementing the method of FIGS. 1 and 2A-2J.

FIG. 3 shows an example of a step S30 for determining whether the channel holes 200 of FIG. 1 have been formed normally. The channel holes 200 are examples of device patterns to which the inventive concept may be applied. Here, therefore, the term "device patterns" may refer to the patterns of or used in the forming of an electronic component such as a semiconductor device.

Referring to FIG. 3, the step S30 for determining whether the channel holes 200 have been formed normally may include producing a pattern image (S310), producing a boundary image (S320), producing an overlapping image (S330), extracting a threshold value (S340), producing a binary image (S350), determining whether binary patterns are symmetrical (S360), and selectively outputting a normal detection signal (S370) and an abnormal detection signal (S380) based on the determination of whether the binary patterns are symmetrical.

Figure 4A:
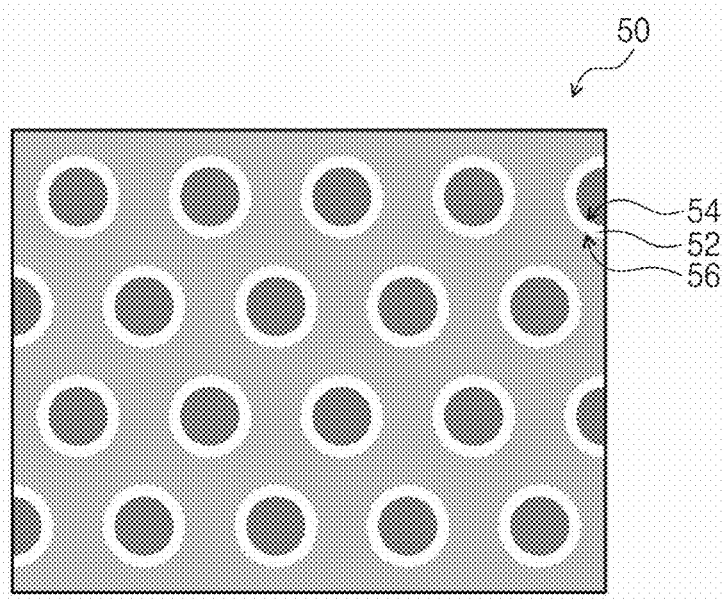
FIGS. 4A, 5A and 6A are, respectively, a pattern image, a boundary image, and an overlapping image produced from the image processing unit shown in FIG. 2C.
Figure 4B:
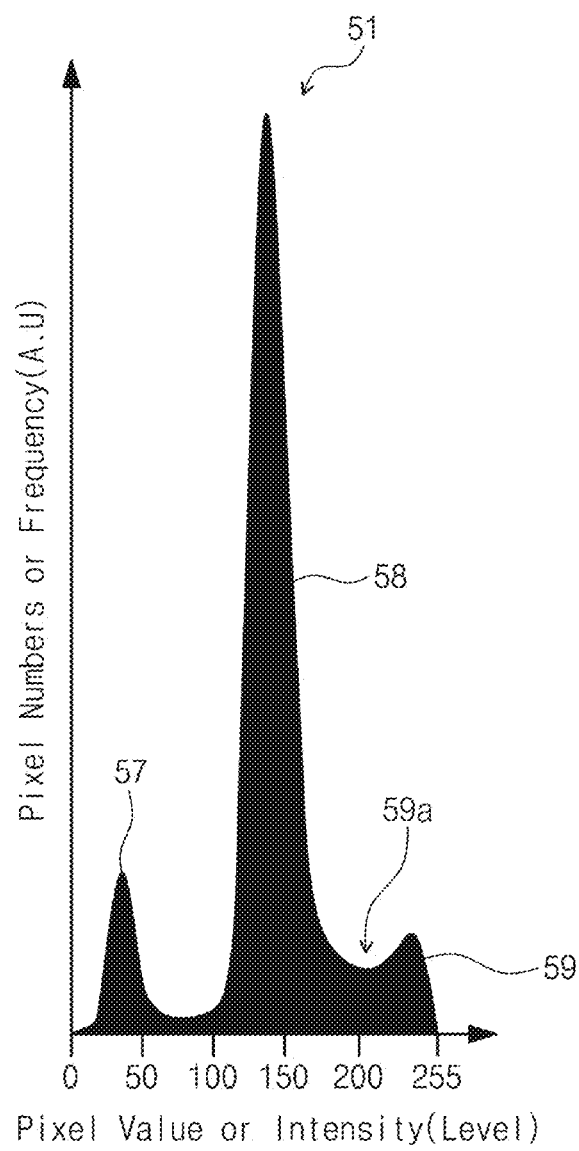
FIGS. 4B, 5B and 6B are graphs illustrating distributions of pixel values of the pattern image, the boundary image, and the overlapping image shown in FIG. 4A to FIG. 6A.
Figure 5A:
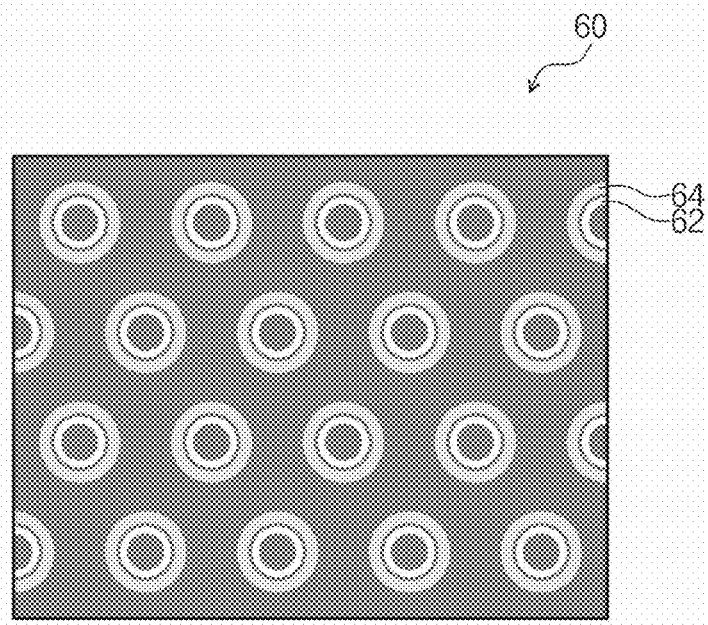
Figure 5B:
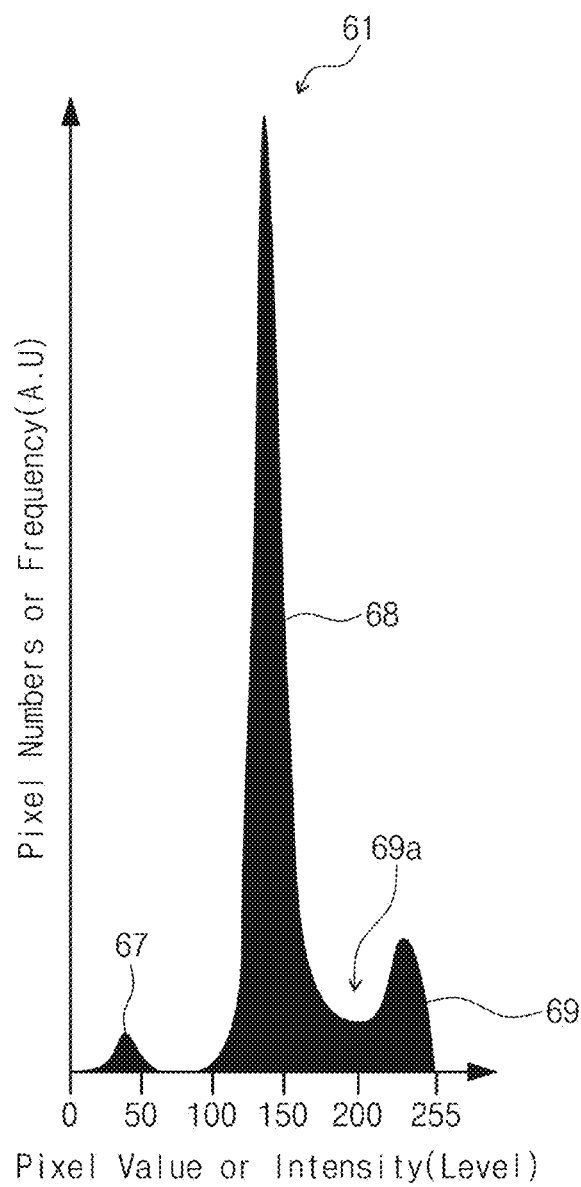
Figure 6A:
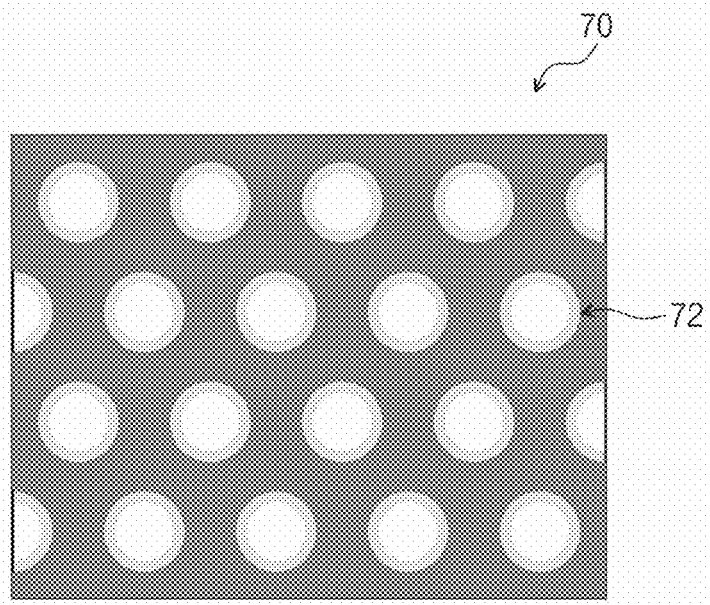
Figure 6B:
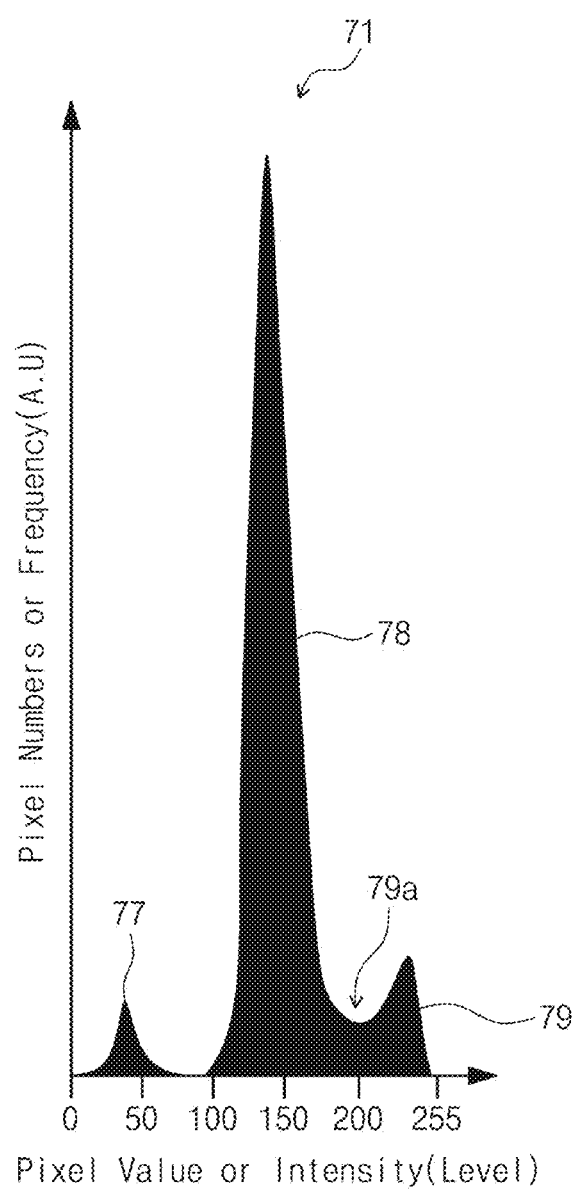

FIGS. 4A, 5A and 6A show a pattern image 50, a boundary image 60, and an overlapping image 70 produced from the image processing unit 44 of FIG. 2C. FIGS. 4B, 5B and 6B are graphs illustrating pixel value distributions 51, 61, and 71 of the pattern image 50, the boundary image 60, and the overlapping image 70 shown in FIGS. 4A, 5A and 6A. To produce the data by which the graphs of FIGS. 4B, 5B and 6B can be created, the pattern image 50, boundary image 60, and overlapping image 70 may be pixelated.

Referring to FIGS. 3 and 4A, the image processing part 44 may produce the pattern image 50 (S310). In an example, the pattern image 50 may be displayed in a gray scale (values of gray shades from black to white). For example, the gray scale may include 256 pixel values (i.e., pixel values 0 to 255), intensity values, or levels. The image processing part 44 may process pixel values of the pattern image 50 in 8-bit data units ($2^8$=256 pixel values=1 byte). In an example, the pattern image 50 may include patterns 52 (or more precisely, virtual images of patterns). In this example, the patterns 52 may correspond to the channel holes 200. For example, each of the patterns 52 may be annular.

Referring to FIG. 4B, a histogram may be displayed to indicate a pixel value distribution 51 of the pattern image 50. In an example, the pixel value distribution 51 of the pattern image 50 may include a first dark pixel value distribution 57, a first gray pixel value distribution 58, and a first bright pixel value distribution 59. The first dark pixel value distribution 57 may include pixel data of, for example, number or frequency of pixels displaying pixel values of 0 to 50 or corresponding intensity levels. The first gray pixel value distribution 58 may include pixel data of, for example, number or frequency of pixels displaying pixel values of 51 to 200 or corresponding intensity levels. The first bright pixel value distribution 59 may include pixel data of, for example, number or frequency or pixels displaying pixel values or corresponding intensity levels of 201 to 255. The first gray pixel value distribution 58 may be larger than the first dark pixel value distribution 57 and the first bright pixel value distribution 59. In an example, a first valley 59a between the first gray and bright pixel value distributions 58 and 59 may be gently rounded. The first valley 59a may fall between pixel values of from about 180 to about 220. For example, the first valley 59a may correspond to a quadratic function whose leading coefficient (referred to hereinafter as a first leading coefficient) is less than 1. The first leading coefficient may be in the range of from about ⅓ to about ½ and may fall precisely within the range of ⅓ to ½.

Referring to FIGS. 4A and 4B, the patterns 52 may have pixel values in the first bright pixel value distribution 59. In other words, the patterns 52 may be indicated by bright pixel values. Dark pixel values may indicate regions inside the patterns 52 in the pattern image 50, and gray pixel values may indicate regions outside of the patterns 52 in the pattern image 50. In an example, each of the patterns 52 may have an inner boundary 54 and an outer boundary 56. The inner boundary 54 may be disposed inside the outer boundary 56. The inner boundary 54 of each of the patterns 52 may be seen more sharply than the outer boundary 56. A difference in sharpness between the inner boundary 54 and the outer boundary 56 may originate due to a difference in gray scale values on opposite sides of the boundary. The inner boundary 54 may be defined by a difference between dark and bright pixel values, and the outer boundary 56 may be defined by a difference between bright and gray pixel values.

Note, the image processing part 44 may remove noise from the pattern image 50. For example, the image processing part 44 may be configured with a Gaussian blur program to remove noise from the pattern image 50.

Referring to FIGS. 3 and 5A, the image processing part 44 may produce the boundary image 60 (S320) by digitally enhancing the pattern image 50. More specifically, the boundary image 60 may be an edge-enhanced image of the patterns 52 in the pattern image 50. A second order derivative filter may be used to produce the boundary image 60. For example, the boundary image 60 may be obtained by a Sobel filter. In an example, the boundary image 60 may include first and second boundary patterns 62 and 64. The first and second boundary patterns 62 and 64 may respectively correspond to the inner and outer boundaries 54 and 56 of each of the patterns 52. The first boundary pattern 62 may be formed inside the second boundary pattern 64. The first boundary pattern 62 may be brighter than the second boundary pattern 64.

Referring to FIG. 5B, a histogram may be displayed to indicate a pixel value distribution 61 of the boundary image 60. The pixel value distribution 61 of the boundary image 60 may correspond to the pixel value distribution 51 of the pattern image 50 shown in FIG. 4A. In an example, the pixel value distribution 61 of the boundary image 60 may include a second dark pixel value distribution 67, a second gray pixel value distribution 68, and a second bright pixel value distribution 69. The second gray pixel value distribution 68 may be larger than the first gray pixel distribution 58 of FIG. 4B. The second bright pixel value distribution 69 may be smaller than the first gray pixel distribution 59 of FIG. 4B. In an example, a second valley 69a between the second gray and bright pixel value distributions 68 and 69 may be gently rounded. The second valley 69a may fall between pixel values of from about 180 to about 220. For example, the second valley 69a may correspond to a quadratic function whose leading coefficient (referred to as hereinafter as a second leading coefficient) is less than 1. The second leading coefficient may be in the range from about ½ to about ⅔ and may fall precisely within the range of ½ to ⅔.

Referring to FIGS. 5A and 5B, the first and second boundary patterns 62 and 64 may be indicated by pixel values in the second bright pixel value distribution 69. A region inside each of the first boundary patterns 62 may be indicated by a pixel value in the second dark pixel value distribution 67. Pixel values in the second gray pixel value distribution 68 may indicate a region outside the second boundary pattern 64 and an intermediate region between the first and second boundary patterns 62 and 64.

Referring to FIGS. 3 and 6A, the image processing part 44 may produce the overlapping image 70 (S330). In an example, the overlapping image 70 may include overlapping patterns 72. For example, each of the overlapping patterns 72 may be an image in which the pattern image 50 and the boundary image 60 are digitally combined and more specifically, are digitally superimposed. A superimposing of the pattern image 50 with the boundary image 60 in effect causes the patterns 52 of the pattern image 50 to overlap the first and second boundary patterns 62 and 64 of the boundary image 60. As a result, for example, images of the patterns 52 contained in the pattern image 50 occupy regions between the boundary patterns 62 and 64.

Referring to FIG. 6B, a histogram may be displayed to indicate a pixel value distribution 71 of the overlapping image 70. The pixel value distribution 71 of the overlapping image 70 may partially include the pixel value distribution 51 of the pattern image 50 and the pixel value distribution 61 of the boundary image 60. In an example, the pixel value distribution 71 of the boundary image 70 may include a third dark pixel value distribution 77, a third gray pixel value distribution 78, and a third bright pixel value distribution 79.

The third dark pixel value distribution 77 may be separated from the third gray pixel value distribution 78 and the third bright pixel value distribution 79. A third valley 79a may be disposed between and connect the third gray and bright pixel value distributions 78 and 79. The third valley 79a may fall between pixel values of from about 180 to about 220. In an example, the third valley 79a may be narrower than the first and second valleys 59a and 69a of FIGS. 4B and 5B. Alternatively, the third valley 79a may be sharper than the first and second valleys 59a and 69a. For example, the third valley 79a may correspond to a quadratic function whose leading coefficient (referred to as hereinafter as a third leading coefficient) is equal to or more than 1. The third leading coefficient may be in the range from about 1 to about 3/2.

Figure 8:
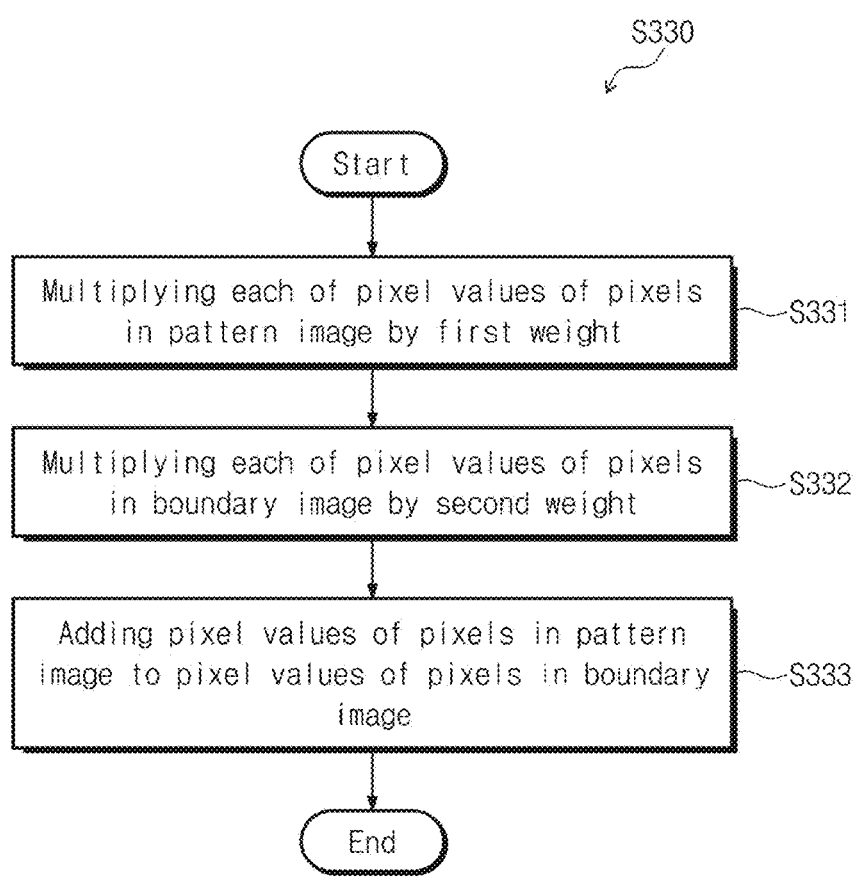
FIG. 8 is a flow chart illustrating an example of producing an overlapping image in the routine of FIG. 3.

FIG. 8 shows an example of the step S330 for producing the overlapping image 70 of FIG. 6A (S330 in FIG. 3).

Referring to FIG. 8, the step S330 for producing the overlapping image 70 may include multiplying each pixel value of pixels in the pattern image 50 by a first weight (S331), multiplying each pixel value of pixels in the boundary image 60 by a second weight (S332), and adding the pixel values of pixels of the pattern image 50 to the pixel values of pixels in the boundary image 60 (S333).

Referring to FIGS. 4A, 4B, and 8, the image processing part 44 may multiply each pixel value of pixels in the pattern image 50 by the first weight (S331). In an example, the first weight may be 0.5 or thereabout. The pattern image 50 may become dark as a whole. Alternatively, the image processing part 44 may multiply the pixel value distribution 51 of the pattern image 50 by the first weight. The number of pixels of the first dark pixel value distribution 57, the first gray pixel value distribution 58, and the first bright pixel value distribution 59 may become reduced by the first weight as a whole.

Referring to FIGS. 5A, 5B, and 8, the image processing part 44 may multiply each pixel value of pixels in the boundary image 60 by the second weight (S332). In an example, the second weight may be the same as the first weight. For example, the second weight may be 0.5 or thereabout. The boundary image 60 may become dark as a whole. Alternatively, the image processing part 44 may multiply the pixel value distribution 61 of the pattern image 60 by the second weight. The number of pixels of the second dark pixel value distribution 67, the second gray pixel value distribution 68, and the second bright pixel value distribution 69 may become reduced by the second weight as a whole.

Referring to FIGS. 6A, 6B, and 8, the image processing part 44 may produce the overlapping image 70 by adding the pixel values of pixels in the pattern image 50 to the pixel values of pixels in the boundary image 60 (S333). The overlapping image 70 may be brighter than the darkened pattern and boundary images 50 and 60. Alternatively, the image processing part 44 may produce the pixel value distribution 71 of the overlapping image 70. The third dark pixel value distribution 77 may be produced by adding the diminished first and second dark pixel value distributions 57 and 67. The third dark pixel value distribution 77 may be narrower than the initial first and second dark pixel value distributions 57 and 67. The third gray pixel value distribution 78 may be produced by adding the diminished first and second gray pixel value distributions 58 and 68. The third gray pixel value distribution 78 may be narrower and taller than the initial first and second gray pixel value distributions 58 and 68. The third bright pixel value distribution 79 may be produced by adding the diminished first and second bright pixel value distributions 59 and 69. The third bright pixel value distribution 79 may be narrower and taller than the initial first and second bright pixel value distributions 59 and 69. Alternatively, the third valley 79a may be lower and narrower than the first and second valleys 59a and 69a.

Figure 9:
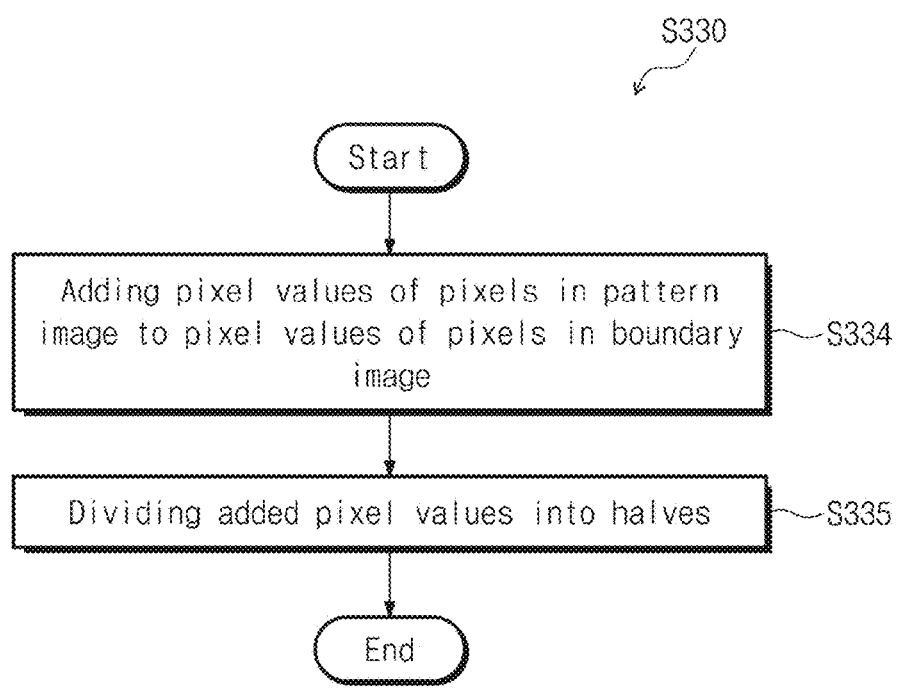
FIG. 9 is a flow chart illustrating an example of producing an overlapping image in the routine of FIG. 3.

FIG. 9 shows another example of the step S330 (FIG. 3) for producing the overlapping image 70 of FIG. ˆA.

Referring to FIG. 9, the step S330 for producing the overlapping image 70 may include adding the pixel values of pixel in the pattern image 50 to the pixel values of pixels in the boundary image 60 (S334) and dividing the added pixel values in half (S335).

Referring to FIGS. 6A, 6B, and 9, the image processing part 44 may add the pixel values of pixel in the pattern image 50 to the pixel values of pixels in the boundary image 60 (S334).

Subsequently, the image processing part 44 may produce the overlapping image 70 by dividing the added values in half (S335).

Referring back to FIGS. 3 and 6B, the image processing part 44 may extract a threshold value (S340). In an example, the threshold value may be extracted in accordance with the pixel value distribution 71 of the overlapping image 70. For example, the threshold value may correspond to a minimum pixel value of the third valley 79a. The minimum pixel value may fall on a vertex of the third valley 79a. The minimum pixel value of the third valley 79a may be calculated more exactly than those of the first and second valleys 59a and 69a. The minimum pixel value of the third valley 79a may reliably establish the threshold value. Accordingly, the likelihood that the electron microscope 10 will produce an error in its image detection or imprecise image data is reduced.

Figure 7:
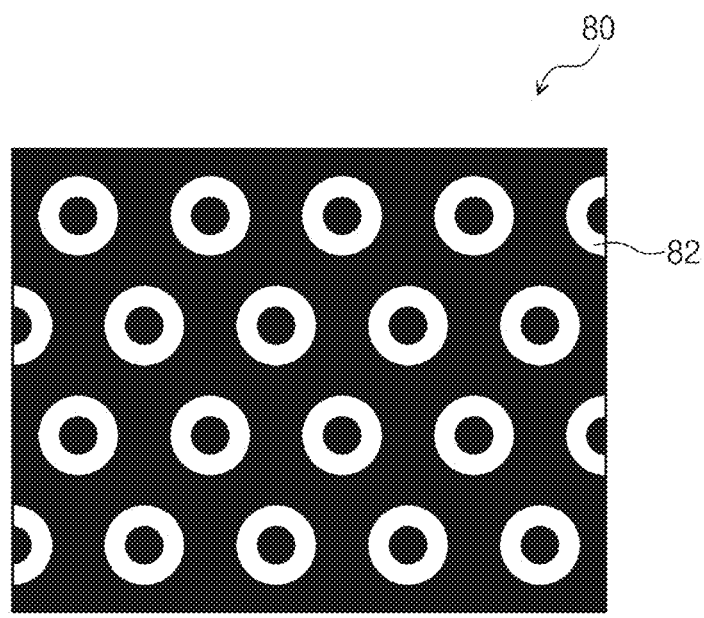
FIG. 7 is a binary image produced from the image processing unit shown in FIG. 2C.

FIG. 7 shows a binary image 80 produced from the image processing part 44 of FIG. 2C.

Referring to FIGS. 3 and 7, the image processing part 44 may produce the boundary image 80 (S350). The binary image 80 may be produced based on the threshold value. The threshold value may be used as a binarization reference value in producing the binary image. For example, when the pixel values of pixels in the overlapping image 70 of FIG. 6A are smaller than the threshold value, the image processing part 44 may cause those pixels to display a dark state in producing the binary image 80. In other words, when the pixel values of pixels in the overlapping image 70 of FIG. 6A are smaller than the threshold value those pixels may have a pixel value of 0 (i.e., black). When the pixel values of pixels in the overlapping image 70 are equal to or greater than the threshold value, those pixels may display a bright state in the binary image 80. In other words, when the pixel values of pixels in the overlapping image 70 of FIG. 6A are equal to or greater than the threshold value the pixels in the binary image 80 may have a pixel value of 1 (i.e., white). In an example, the binary image 80 may include binary patterns 82. The binary patterns 82 may correspond to the overlapping patterns 72 of FIG. 6A. For example, each of the binary patterns 82 may be annular.

Next, the image processing part 44 may determine whether each of the binary patterns 82 is symmetrical (S360). To this end, the image processing part 44 may be configured with image recognition or analysis software.

Referring to FIGS. 2C, 3, and 7, when each of the binary patterns 82 is symmetrical, the image processing part 44 outputs a normal detection signal (S370). In an example, symmetry is determined to exist when each of the binary patterns 82 is symmetrical about its geometric center. For example, when the binary patterns 82 are circular, the image processing part 44 determines that the channel holes 200 have been formed normally.

On the other hand, when at least one of the binary patterns 82 is asymmetrical, the image processing part 44 may output an abnormal detection signal (S380). In an example, one or more of the binary patterns 82 may be determined to be asymmetrical about its geometric center. For example, when the binary patterns 82 have the shape of an oval ring, the image processing part 44 may determine that the channel holes 200 are formed abnormally. In this case, the channel holes 200 may have a bending failure. The image processing part 44 may display an indication of such channel hole failure.

Referring back to FIG. 1, when it is determined that the channel holes 200 are abnormally formed, the thin-film structure TS may be removed (S40). For example, a wet etching process may be performed to remove the thin-layer structure TS. Alternatively, a chemical mechanical polishing process may be performed to remove the thin-layer structure TS. After that, steps of forming the thin-layer structure (S10), forming the channel holes 200 (S20), and determining whether the channel holes 200 are formed normally (S30) may be carried out again.

Figure 2D:
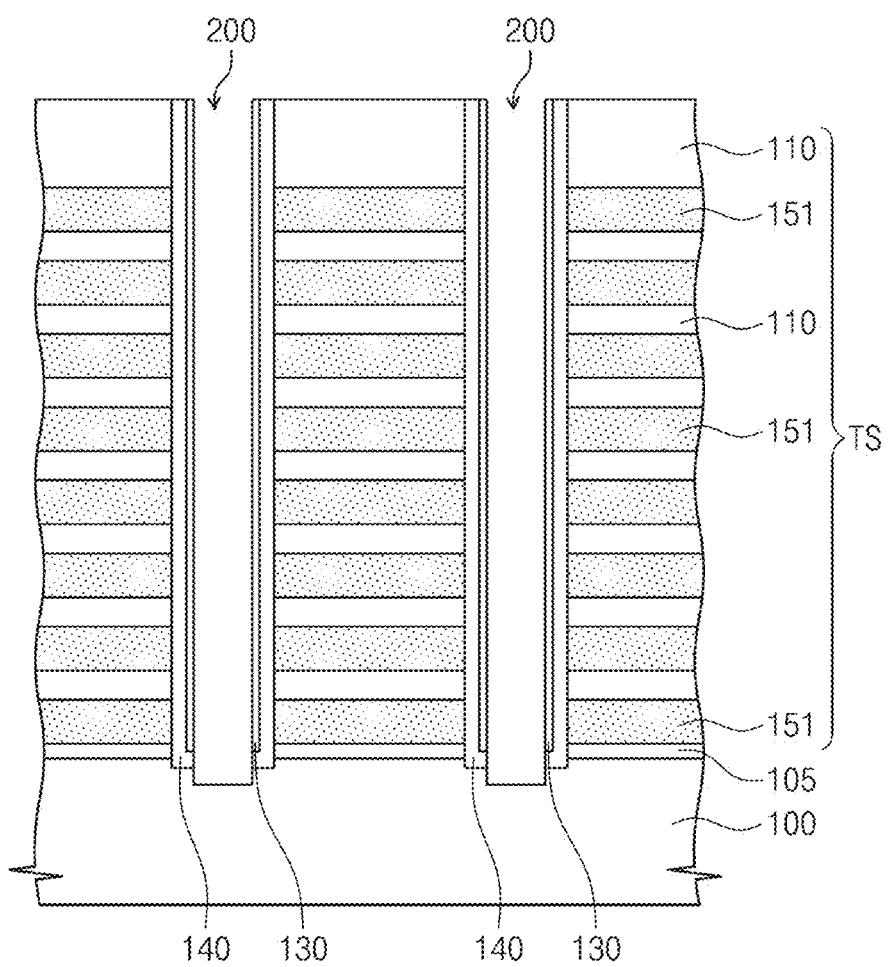

Referring to FIGS. 1 and 2D, when it is determined that the channel holes 200 are normally formed, vertical insulators 140 and first semiconductor patterns 130 may be formed on inner walls of the channel holes 200 (S50). In more detail, a vertical insulation layer and a first semiconductor layer may be conformally formed on the substrate 100 and the inner walls defining the channel holes 200. The vertical insulation layer and the first semiconductor layer may be deposited by a plasma enhanced CVD process, a physical CVD process, or an ALD process.

The vertical insulation layer may include a charge storage layer used as a memory element of a flash memory device. For example, the charge storage layer may be a trap insulation layer or an insulation layer including conductive nanodots. Alternatively, the vertical insulation layer may include a thin film for a phase change memory device or variable resistance memory device. In an example, the vertical insulation layer may include a blocking insulation layer, a charge storage layer, or a tunnel insulation layer. The blocking insulation layer may cover sidewalls of the sacrificial layers 151, sidewalls of the upper insulation layers 110, and the top surface of the substrate 100 exposed through the channel holes 200. The blocking insulation layer may include silicon oxide. The charge storage layer may include a trap insulation layer or an insulation layer including conductive nanodots. For example, the charge storage layer may include at least one of silicon nitride, silicon oxynitride, silicon-rich nitride, nanocrystalline silicon, and a laminated trap layer. The tunnel insulation layer may be of material having a band gap greater than that of the charge storage layer. For example, the tunnel insulation layer may be silicon oxide.

The first semiconductor layer may be formed on the vertical insulation layer. For example, the first semiconductor layer may be polycrystalline silicon, single crystalline silicon, or amorphous silicon.

After the vertical insulation layer and the first semiconductor layer are sequentially formed, the first semiconductor layer and the vertical insulation layer may be anisotropically etched to partially expose the substrate 100. Accordingly, the first semiconductor patterns 130 and the vertical insulators 140 may be formed on inner walls defining the channel holes 200. The vertical insulators 140 and the first semiconductor patterns 130 may have a cylindrical shape whose opposite ends are open. In the process of anisotropically etching the first semiconductor layer and the vertical insulation layer, the top surface of the substrate 100 may be etched, i.e., an over-etch may occur.

Moreover, as a result of the anisotropic etching of the first semiconductor layer and the vertical insulation layer, the top surface of the thin-layer structure TS may be exposed. Accordingly, the first semiconductor patterns 130 and the vertical insulators 140 may be formed locally in the channel holes 200.

Figure 2E:
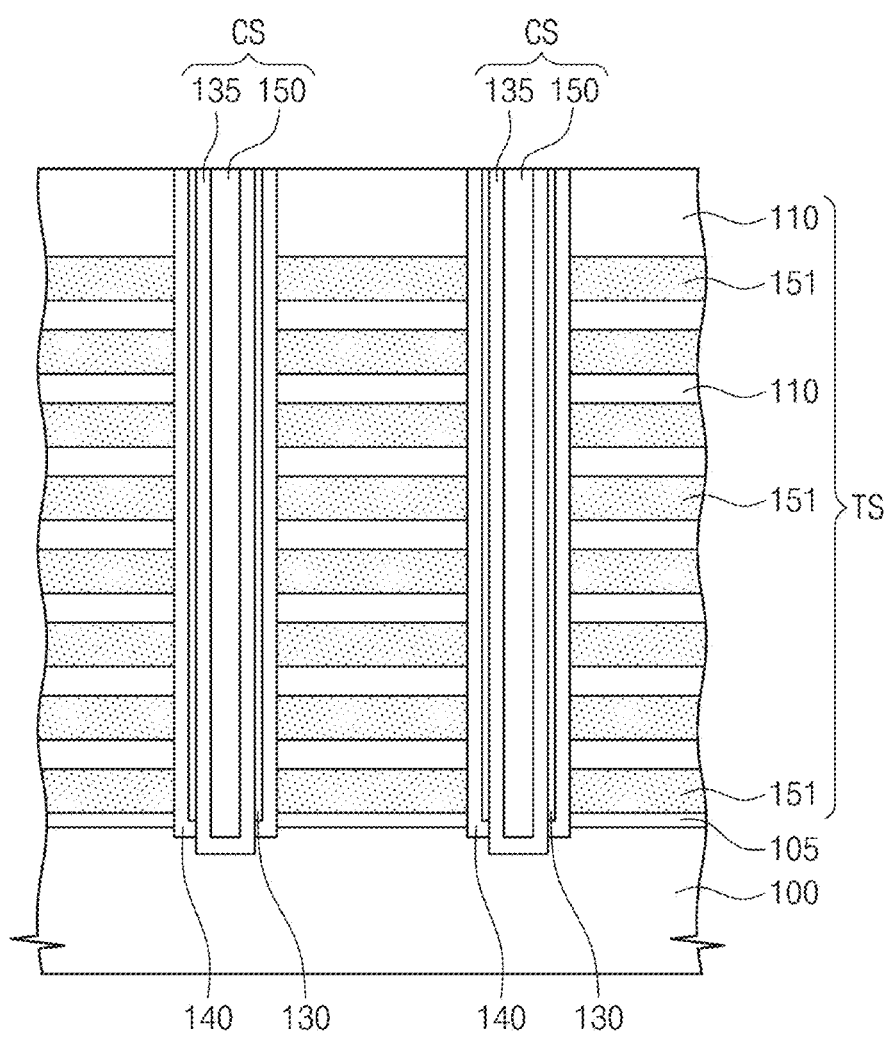

Referring to FIGS. 1 and 2E, channel structures CS may be formed on the vertical insulators 140, the first semiconductor patterns 130, and the substrate 100 in the channel holes 200 (S60). Each of the channel structures CS may include a second semiconductor pattern 135 and a vertical insulation pattern 150. For example, the second semiconductor patterns 135 and the vertical insulation patterns 150 may be formed by depositing a second semiconductor layer and an insulation layer and then planarizing the second semiconductor layer and the insulation layer. In more detail, the second semiconductor layer and the insulation layer may be sequentially formed on the substrate 100. The second semiconductor layer may be conformally formed to have a thickness so as not to completely fill the channel holes 200. The second semiconductor layer may include a semiconductor material (e.g., polycrystalline silicon, single crystalline silicon, or amorphous silicon) formed using one of an atomic layer deposition (ALD) technology and a chemical vapor deposition (CVD) technology. The insulation layer may be formed to completely fill the channel holes 200. The insulation layer may be one of silicon oxide and an insulating material formed using a spin-on-glass (SOG) technology. Subsequently, the second semiconductor layer and the insulation layer may be planarized to expose the top surface of the thin-layer structure TS, so that the second semiconductor patterns 135 and the vertical insulation patterns 150 may be formed locally in the channel holes 200.

The channel holes 200 may be provided therein with the second semiconductor patterns 135 formed to have a pipe shape whose one end is closed, a hollow cylindrical shape whose one end is closed, or a cup shape. Alternatively, the second semiconductor patterns 135 may be formed to have a pillar shape that fills the channel holes 200.

The vertical insulation patterns 150 may be formed to fill the channel holes 200.

Figure 2F:
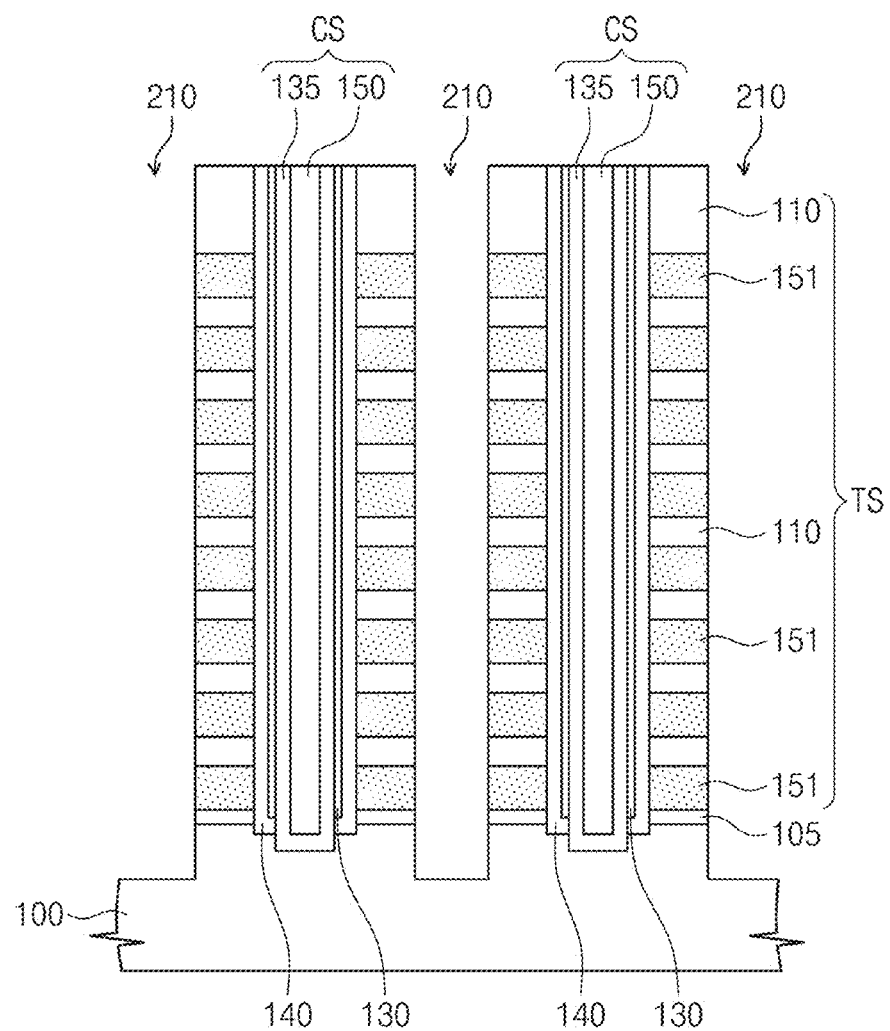

Referring to FIGS. 1 and 2F, trenches 210 may be formed by etching the thin-layer structure TS between the channel holes 200 (S70). The trenches 210 may partially expose the substrate 100.

Figure 2G:
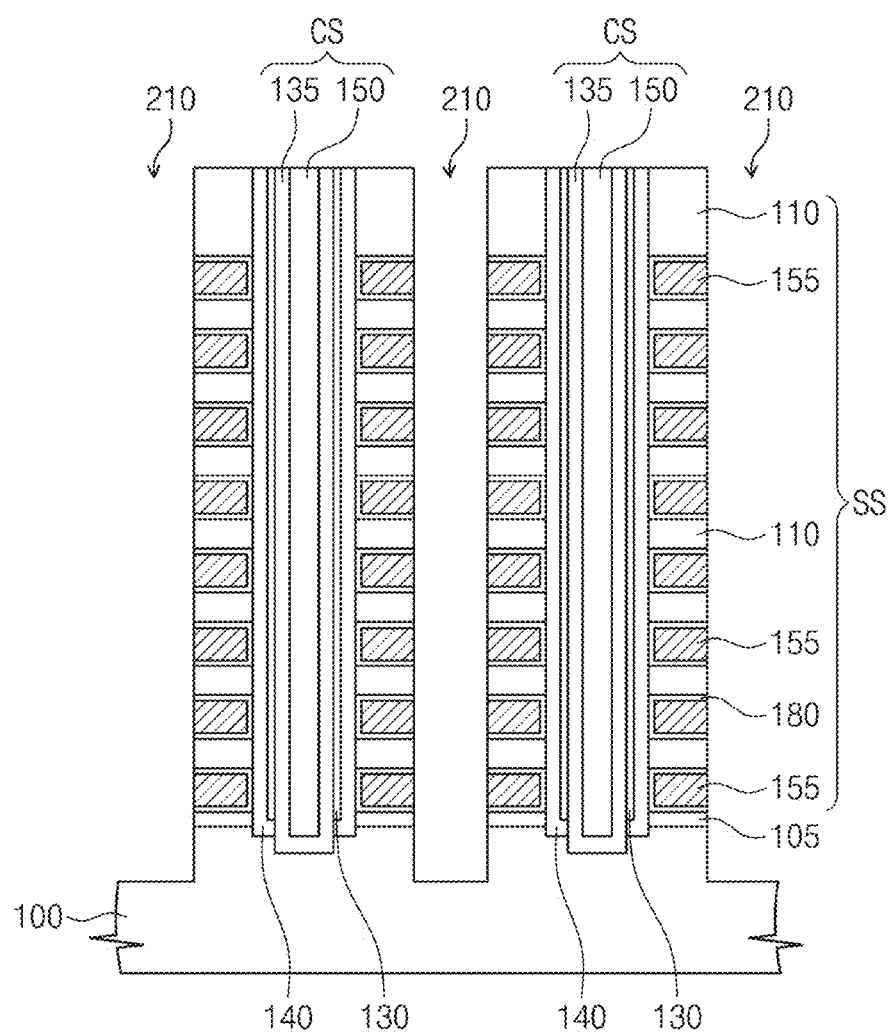

Referring to FIGS. 1 and 2G, recesses may be formed by removing the sacrificial layers 151 exposed through the trenches 210, and horizontal insulators 180 and gate electrodes 155 may be formed in the recesses (S80). The recesses may be gaps extending horizontally from the trenches 210 and formed to expose parts of sidewalls of the vertical insulators 140.

The horizontal insulators 180 may be formed to line the recesses.

The gate electrodes 155 may be formed to fill the remainder of the recesses in which the horizontal insulators 180 have been formed. The forming of the horizontal insulators 180 and the gate electrodes 155 may include sequentially forming a horizontal layer and a gate layer (e.g., a metal layer) sequentially filling the recesses and removing the horizontal layer and the gate layer from the trenches 210. The horizontal insulators 180 may include a data storage layer. Similarly to the vertical insulators 140, the horizontal insulators 180 may include a single thin layer or a plurality of thin layers. In an example, the horizontal insulators 180 may include a blocking dielectric layer of a charge trap type nonvolatile memory transistor.

As a result, a stack structure SS in which the gate electrodes 155 and the upper insulation layers 110 are stacked may be formed.

Figure 2H:
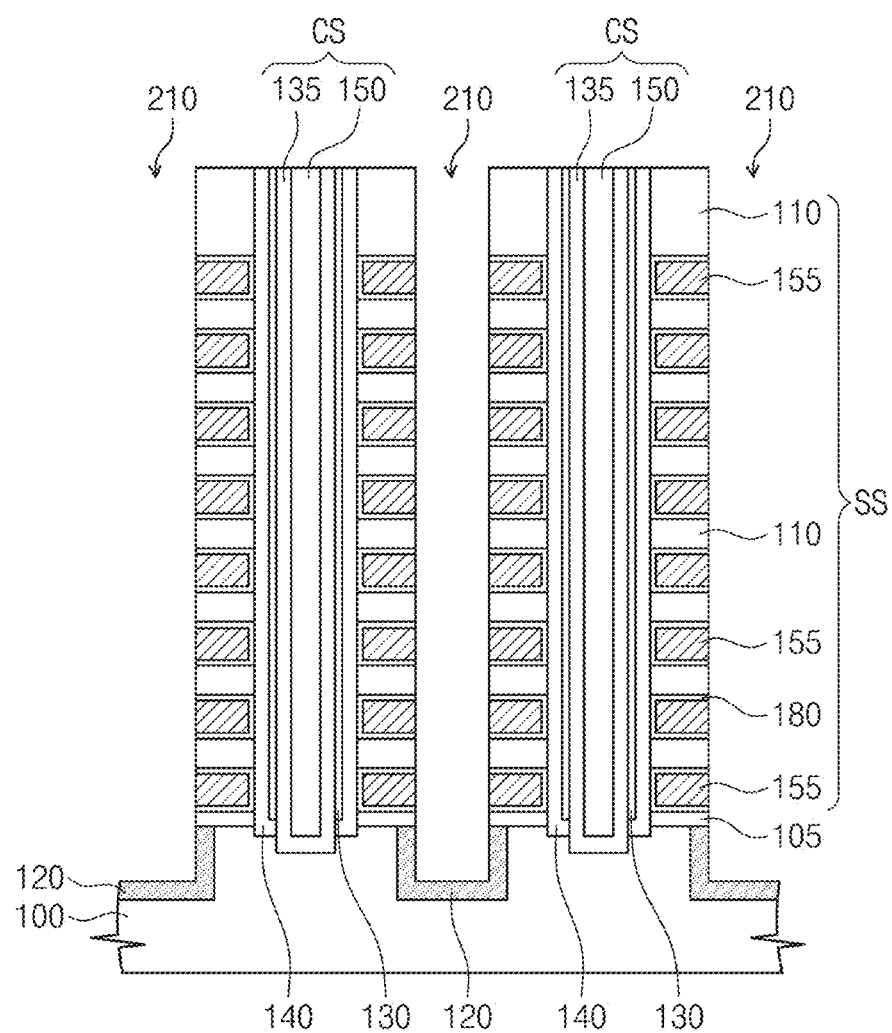

Referring to FIGS. 1 and 2H, common source regions 120 may be formed on the substrate 100 in the trenches 210 (S90). The common source regions 120 may be formed by implanting ions in portions of the substrate 100 that are exposed through the trenches 210. The common source regions 120 may constitute PN junctions with the substrate 100. In an example, the common source regions 120 may be connected to each other to have the same electrical potential state. Alternatively, the common source regions 120 may be electrically separated to have electrical potentials different from each other. In an example, the common source regions 120 may constitute a plurality of source groups electrically independent of each other, each source group including a plurality of the common source groups, such that the plurality of source groups may be electrically separated to have electrical potentials different from each other.

Figure 2I:
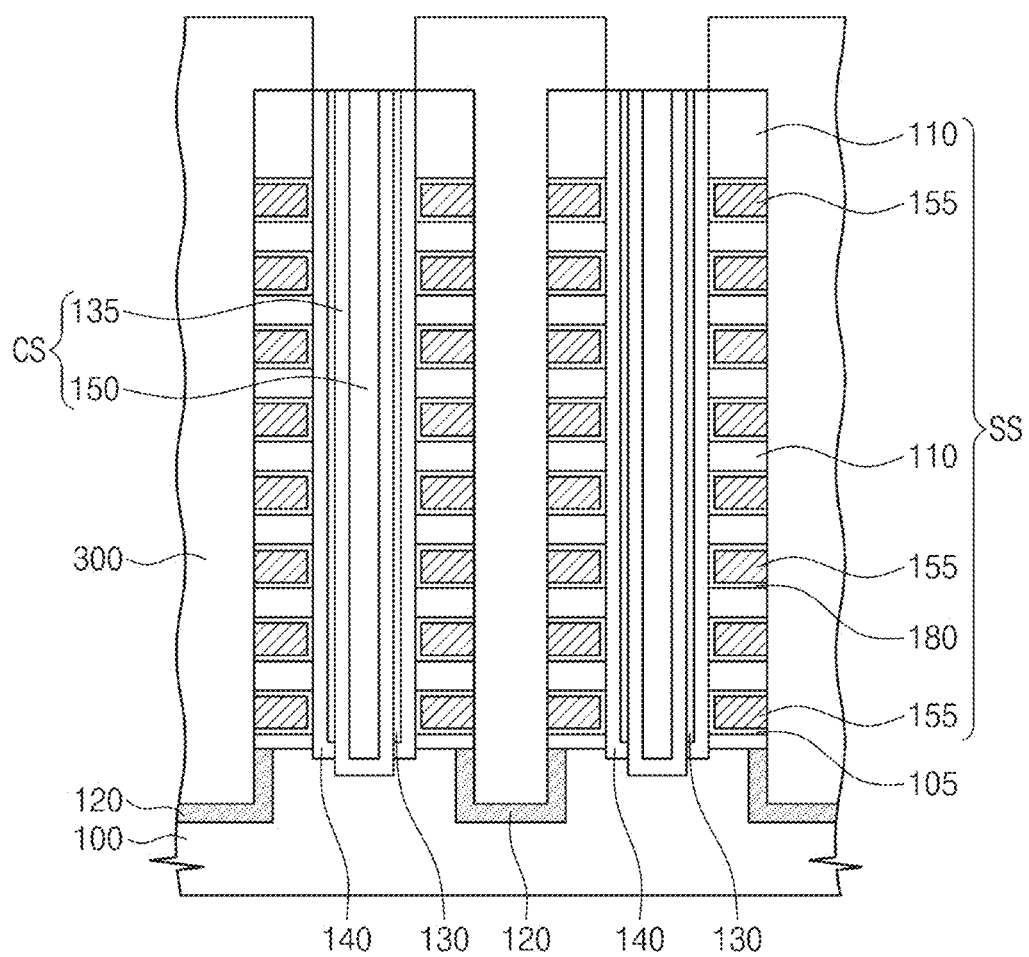

Referring to FIGS. 1 and 2I, electrode separation patterns 300 may be formed in the trenches 210 (S100). The electrode separation patterns 300 may be formed of at least one of silicon oxide, silicon nitride, and silicon oxynitride. For example, the electrode separation patterns 300 may be patterned by a photolithography process or an etching process. The channel structures CS may be spaced from the electrode separation patterns 300.

Figure 2J:
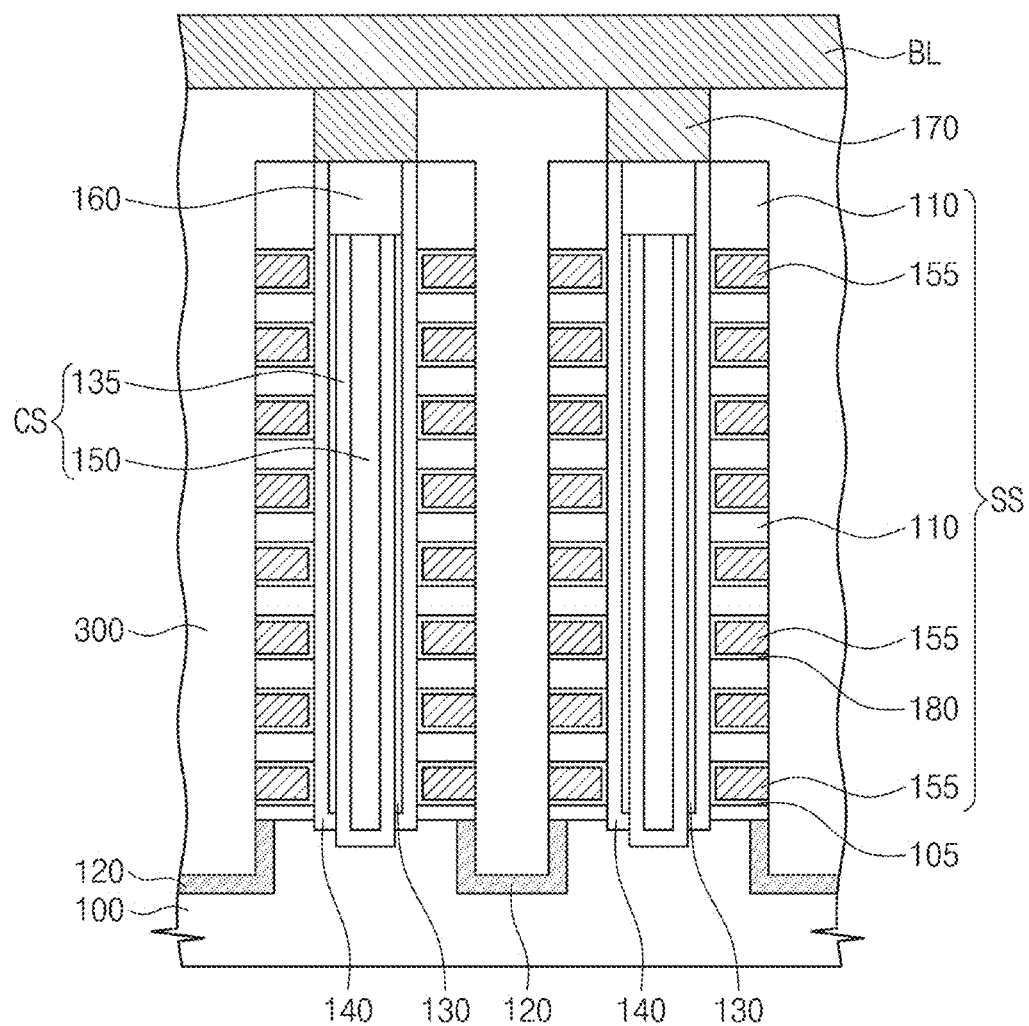

Referring to FIGS. 1 and 2J, conductive pads 160, contact plugs 170, and a bit line BL may be formed (S110). The conductive pads 160 may be connected to the first semiconductor patterns 130 and the second semiconductor patterns 135. For example, the conductive pads 160 may be formed by recessing upper portions of the first and second semiconductor patterns 130 and 135 and then filling the resulting recesses with conductive material. Alternatively, the conductive pads 160 may be formed by doping upper portions of the channel structures CS with impurities having conductivity different from those of the first and second semiconductor patterns 130 and 135 positioned below the conductive pads 160.

The contact plugs 170 may be formed on the conductive pads 160. The bit line BL may be formed on the contact plugs 170 and the electrode separation pattern 300. The bit line BL may be electrically connected through the contact plugs 170 to the first and second semiconductor patterns 130 and 135.

The method of measuring a pattern according to the present inventive concept may include producing the pattern image, producing the boundary image, producing the overlapping image, extracting the binary threshold value, and producing the binary image. The threshold value of the binary image may be set by the minimum pixel value of the valley between the gray and bright pixel value distributions of a histogram of the overlapping image. The minimum pixel value of the valley between the gray and bright pixel value distributions of the histogram of the overlapping image can be exactly calculated, so that it may be possible to increase reliability of establishing the threshold value. It may also possible to reduce an image detection error of the electron microscope.

Although the inventive concept has been described in connection with examples illustrated in the accompanying drawings, it will be understood to those skilled in the art that various changes and modifications may be made without departing from the technical spirit and scope of the inventive concept. It therefore will be understood that the examples described above are illustrative but not limitative with respect to the inventive concept.

What is claimed is:

1. An image processing method of inspecting patterns, the method comprising:

capturing a pattern image of patterns by irradiating the patterns with a beam providing unit and detecting resulting emissions from the patterns, wherein the patterns contained in the pattern image each correspond to a respective one of patterns being inspected and each have first and second boundaries;

enhancing the first and second boundaries in the pattern image to produce a boundary-enhanced image including first and second boundary patterns corresponding to the first and second boundaries, by processing the pattern image using an image processor;

combining the pattern image and the boundary-enhanced image, using the image processor, to produce an overlapping image including overlapping patterns in which images of the patterns contained in the pattern image occupy regions between the boundary patterns;

binarizing the overlapping image, using the image processor, to produce a binary image including binary patterns corresponding to the overlapping patterns; and graphically analyzing the binary image, using the image processor, to determine whether patterns used to produce the pattern image have a defect.

2. The method of claim 1, further comprising producing a pixel value distribution representative of the overlapping image, and extracting a threshold value for use as a binarization reference value for producing the binary image, wherein the threshold value is extracted from the pixel value distribution representative of the overlapping image.

3. The method of claim 2, wherein the pixel value distribution comprises a first gray pixel value distribution and a first bright pixel value distribution, the threshold value corresponding to a minimum pixel value of a valley between the first gray pixel value distribution and the first bright pixel value distribution.

4. The method of claim 3, wherein the valley conforms to a quadratic function whose leading coefficient is equal to or greater than 1.

5. The method of claim 2, further comprising producing a pixel value distribution representative of the pattern image and a pixel value distribution representative of the boundary-enhanced image, wherein the pixel value distribution representative of the overlapping image is produced by adding the pixel value distribution representative of the pattern image to the pixel value distribution representative of the boundary-enhanced image.

6. The method of claim 5, wherein the pixel value distribution representative of the pattern image comprises a second gray pixel value distribution, a second bright pixel value distribution, and a second valley between the second gray pixel value distribution and the second bright pixel value distribution, and the pixel value distribution representative of the boundary-enhanced image comprises a third gray pixel value distribution, a third bright pixel value distribution, and a third valley between the third gray pixel value distribution and third bright pixel value distribution, each of the second and third valleys conforming to a quadratic function whose leading coefficient is less than 1.

7. The method of claim 1, wherein producing the overlapping image comprises:

multiplying each of pixel values of pixels of the pattern image by a first weight;

multiplying each of pixel values of pixels of the boundary-enhanced image by a second weight; and adding the pixel values of pixels of the pattern image to the pixel values of pixels of the boundary-enhanced image.

8. The method of claim 7, wherein each of the first and second weights is 0.5.

9. The method of claim 1, wherein producing the overlapping image comprises:

adding pixel values of first pixels of the pattern image to pixel values of second pixels of the boundary-enhanced image, respectively, to obtain sums of pixel values; and dividing each of the sums in half.

10. The method of claim 1, wherein each of the patterns contained in the pattern image is annular, and the first and second boundaries respectively comprise inner and outer boundaries each being annular.

11. A method of manufacturing a semiconductor device, the method comprising:

forming a thin-layer structure on a substrate;

etching a portion of the thin-layer structure to form channel holes; and inspecting the channel holes to determine whether the channel holes have been formed normally, wherein inspecting the channel holes comprises:

using an electron microscope having an electron beam source, a secondary electron detector, and a controller including an image processor to capture a pattern image of patterns by irradiating the channel holes with an electron beam from the electron beam source and capturing secondary electrons emitted from the channel holes with the secondary electron detector, wherein the patterns contained in the pattern image each correspond to a respective one of the channel holes and each have first and second boundaries, enhancing the first and second boundaries in the pattern image to produce a boundary-enhanced image including first and second boundary patterns corresponding to enhanced images of the first and second boundaries, by processing the pattern image using an image processor, combining the pattern image and the boundary-enhanced image, using the image processor, to produce an overlapping image including overlapping patterns in which images of the channel holes contained in the pattern image occupy regions between the boundary patterns, binarizing the overlapping image to produce a binary image including binary patterns corresponding to the overlapping patterns, and graphically analyzing the binary image, using the image processor, to determine whether patterns used to produce the pattern image have a defect.

12. The method of claim 11, further comprising:

determining whether the binary patterns are symmetrical; and when the binary patterns are asymmetrical, outputting an abnormal detection signal to denote a failure in a process of forming the channel holes, wherein the method further comprises removing the thin-layer structure.

13. The method of claim 11, further comprising:

determining whether the binary patterns are symmetrical; and when the binary patterns are asymmetrical, outputting a normal detection signal to denote the channel holes have been formed normally, wherein the method further comprises forming vertical insulators and first semiconductor patterns on the substrate and along sides of the channel holes.

14. The method of claim 13, wherein the normal detection signal is output when the binary patterns each have a circular shape.

15. The method of claim 12, wherein the abnormal detection signal is output when at least one of the binary patterns has an oval shape.

16. A method of manufacturing a semiconductor device, the method comprising:

forming patterns on a substrate; and inspecting the patterns including by:

imaging the substrate to produce a pattern image containing images representative of the patterns, respectively, each of the images having discernible regions demarcated by first and second boundaries, enhancing the first and second boundaries in the pattern image to produce a boundary-enhanced image, wherein the boundary-enhanced image includes first and second boundary patterns as image enhancements of the first and second boundaries demarcating the regions of the images contained in the pattern image, digitally combining the pattern image and the boundary-enhanced image to produce an overlapping image, wherein the overlapping image includes overlapping patterns representative of a superimposing of the images contained in the pattern image with the boundary patterns, respectively, processing the overlapping image to produce a binary image of the overlapping image, wherein the binary image includes binary patterns corresponding to the overlapping patterns, and graphically analyzing the binary image to determine whether the patterns on the substrate have been formed according to specifications.

17. The method of claim 16, wherein the inspecting of the patterns comprises pixelating the overlapping image, producing a histogram of a distribution of values of pixels of the overlapping image, and extracting a threshold value for use in producing the binary image from the histogram.

18. The method of claim 16, wherein the pattern image includes grey-scale images representative of the patterns on the substrate, and the analyzing of the binary image determines whether each of the binary patterns of the binary image has a specified symmetry.

19. The method of claim 16, further comprising selectively performing a manufacturing routine or a re-fabricating routine depending on results of the analyzing of the binary image, wherein the manufacturing routine when performed completes the semiconductor device and the re-fabricating routine when performed removes the patterns on the substrate and subsequently forms new patterns on the substrate.

20. The method of claim 19, wherein the forming patterns on a substrate comprises forming a stack of layers on the substrate, and etching a portion of the stack to form channel holes extending vertically in the stack, the analyzing of the binary image determines whether each of the binary patterns of the binary image have a specified symmetry, and the selectively performing the manufacturing routine and the re-fabricating routine comprises forming vertical insulators and first semiconductor patterns on the substrate and along sides of the channel holes when the binary patterns are determined to each have the specified symmetry, and removing the stack from the substrate when at least on the binary patterns is determined to not have the specified symmetry.

* * * * *